(12) United States Patent
Furuya et al.

(10) Patent No.: US 12,411,116 B2
(45) Date of Patent: Sep. 9, 2025

(54) APPARATUS WITH GAS DETECTION FUNCTION

(71) Applicant: Asahi Kasei Microdevices Corporation, Tokyo (JP)

(72) Inventors: Takaaki Furuya, Tokyo (JP); Naoya Ugomori, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 408 days.

(21) Appl. No.: 18/163,282

(22) Filed: Feb. 2, 2023

(65) Prior Publication Data
US 2023/0243796 A1   Aug. 3, 2023

(30) Foreign Application Priority Data

Feb. 2, 2022  (JP) ................................. 2022-015244
Jan. 25, 2023 (JP) ................................. 2023-009604

(51) Int. Cl.
  *G01N 33/00*   (2006.01)
  *G01N 29/036*  (2006.01)
  *G01N 29/24*   (2006.01)

(52) U.S. Cl.
  CPC ......... *G01N 33/005* (2013.01); *G01N 29/036* (2013.01); *G01N 29/2431* (2013.01);
  (Continued)

(58) Field of Classification Search
  CPC .............. G01N 33/005; G01N 29/036; G01N 29/2431; G01N 2291/021; G01N 2291/02809; G01N 29/222
  See application file for complete search history.

(56) References Cited

U.S. PATENT DOCUMENTS

| | | | | |
|---|---|---|---|---|
| 6,378,372 B1 * | 4/2002 | Karr | ....................... | G01N 29/36 |
| | | | | 73/24.01 |
| 2003/0037801 A1 * | 2/2003 | Bailey | ................. | H01L 21/6875 |
| | | | | 134/1 |

(Continued)

FOREIGN PATENT DOCUMENTS

| | | |
|---|---|---|
| JP | S5334581 A | 3/1978 |
| JP | S5954950 A | 3/1984 |

(Continued)

*Primary Examiner* — Francis C Gray
(74) *Attorney, Agent, or Firm* — KENJA IP LAW PC

(57) ABSTRACT

Provided is an apparatus with a gas detection function capable of detecting a detection target gas with high accuracy. An apparatus with a gas detection function comprises: a housing (10); a vibration source (20); and a gas measurement unit (40) located inside the housing and demarcated by a partition, wherein the vibration source is located outside the gas measurement unit, the gas measurement unit includes a detector (41) located on a substrate (30), and a gas detection space (42) provided with a hole (43) through which a gas passes, and a frequency f expressed by the following Formula (1):

$$f = \frac{c}{2\pi}\sqrt{\frac{S}{VL}} \qquad \text{Formula (1)}$$

is 500 Hz or more, where V is a volume of the gas detection space, S is a cross-sectional area of the hole, L is an effective length of the hole, and c is a sound speed.

20 Claims, 5 Drawing Sheets

(52) U.S. Cl.
CPC ............... *G01N 2291/021* (2013.01); *G01N 2291/02809* (2013.01)

(56) References Cited

U.S. PATENT DOCUMENTS

| | | | |
|---|---|---|---|
| 2010/0263437 A1* | 10/2010 | Koyama | G01N 29/2443 73/64.53 |
| 2015/0097663 A1 | 4/2015 | Sloo et al. | |
| 2015/0338390 A1* | 11/2015 | Anglin, Jr. | G01N 27/227 73/23.3 |
| 2017/0176330 A1* | 6/2017 | Lahti | G01N 33/497 |

FOREIGN PATENT DOCUMENTS

| | | | | |
|---|---|---|---|---|
| JP | H06510870 | A | 12/1994 | |
| JP | H0783756 | A | 3/1995 | |
| JP | 2006138752 | A | 6/2006 | |
| JP | 2019091489 | A | 6/2019 | |
| WO | 9215088 | A1 | 9/1992 | |
| WO | WO-2016109781 | A1 * | 7/2016 | ......... G01N 33/0036 |

* cited by examiner

FIG. 5

APPARATUS WITH GAS DETECTION FUNCTION

CROSS-REFERENCE TO RELATED APPLICATION

The present application claims priority to and the benefit of Japanese Patent Application No. 2022-015244 filed Feb. 2, 2022 and Japanese Patent Application No. 2023-009604 filed Jan. 25, 2023, the entire contents of which are incorporated herein by reference.

TECHNICAL FIELD

The present disclosure relates to an apparatus with a gas detection function.

BACKGROUND

Gas sensors that detect gas are used in various fields. With the progress of semiconductor technology and MEMS technology, gas sensors are increasingly miniaturized, and mounting of gas sensors in housings of apparatuses that emit sound, such as smart home devices, is promoted (see, for example, PTL 1).

CITATION LIST

Patent Literature

PTL 1: JP 2019-91489 A

SUMMARY

In the apparatus disclosed in PTL 1, the gas sensor is exposed to air vibration such as music and voice coming from the speaker in the same housing. The gas sensor is also exposed to air vibration from the motor of the air conditioner or the like. These may cause the resonance of the gas in the gas sensor and excite vibration. Noise caused by such vibration degrades the detection accuracy of the gas sensor. In the case where the light source, detector, etc. used in the gas sensor include microstructures suspended in the air using MEMS technology, the influence of noise caused by vibration is particularly significant, and the detection accuracy is likely to degrade greatly.

It could therefore be helpful to provide an apparatus with a gas detection function capable of detecting a detection target gas (i.e. a gas to be detected) with high accuracy.

[1] An apparatus with a gas detection function according to an embodiment of the resent disclosure comprises: a housing; a vibration source; and a gas measurement unit located inside the housing and demarcated by a partition, wherein the vibration source is located outside the gas measurement unit, the gas measurement unit includes a detector located on a substrate, and a gas detection space provided with a hole through which a gas passes, and a frequency f expressed by the following Formula (1):

$$f = \frac{c}{2\pi}\sqrt{\frac{S}{VL}} \qquad \text{Formula (1)}$$

is 500 Hz or more, where V is a volume of the gas detection space, S is a cross-sectional area of the hole, L is an effective length of the hole, and c is a sound speed.

[2] As an embodiment of the resent disclosure, in [1], the hole is provided with a vent pipe, and the effective length is given by the following Formula (2):

$$L=L'+1.5a \qquad \text{Formula (2),}$$

where L' is a total length of the hole and the vent pipe, and a is a radius of the hole.

[3] As an embodiment of the resent disclosure, in [1], the hole is provided with a vent pipe, an exit of the hole and the vent pipe is flat, and the effective length is given by the following Formula (3):

$$L=L'+1.7a \qquad \text{Formula (3),}$$

where L' is a total length of the hole and the vent pipe, and a is a radius of the hole.

[4] As an embodiment of the resent disclosure, in [1], the hole is provided with a vent pipe, a cross-sectional shape of the hole and the vent pipe is irregular, and the effective length is given by the following Formula (4):

$$L=L'+\sqrt{S_{out}} \qquad \text{Formula (4),}$$

where L' is a total length of the hole and the vent pipe, and $S_{out}$ is an area of an exit opening of the hole and the vent pipe.

[5] As an embodiment of the resent disclosure, in any of [1] to [4], the frequency f is 1.0 kHz or more.

[6] As an embodiment of the resent disclosure, in any of [1] to [5], the frequency f is 2.0 kHz or more.

[7] An apparatus with a gas detection function according to an embodiment of the resent disclosure comprises: a housing; a vibration source; and a gas measurement unit located inside the housing, wherein the gas measurement unit includes a detector located on a substrate, and a gas detection space provided with a hole through which a gas passes, the hole is provided with a vent pipe, a cross-sectional shape of the hole and the vent pipe is irregular, an effective length L of the hole is given by the following Formula (5):

$$L=L'+\sqrt{S_{out}} \qquad \text{Formula (5),}$$

where L' is a total length of the hole and the vent pipe, and $S_{out}$ is an area of an exit opening of the hole and the vent pipe, and a frequency f expressed by the following Formula (6):

$$f = \frac{c}{2\pi}\sqrt{\frac{S}{VL}} \qquad \text{Formula (6)}$$

is 100 Hz or less, where V is a volume of the gas detection space, S is a cross-sectional area of the hole, and c is a sound speed.

[8] As an embodiment of the resent disclosure, in any of [1] to [7], the vibration source or the detector is located at a plane of symmetry of a rectangular parallelepiped approximately defined for the housing.

[9] As an embodiment of the resent disclosure, in any of [1] to [8], the vibration source or the detector is located at an axis of symmetry of a cylinder approximately defined for the housing.

[10] As an embodiment of the resent disclosure, in any of [1] to [9], the vibration source or the detector is located at a center point of a sphere approximately defined for the housing.

[11] As an embodiment of the resent disclosure, in any of [1] to [10], the vibration source or the detector is located at an end of a rectangle approximately defined for the substrate.

[12] As an embodiment of the resent disclosure, in any of [1] to [11], a frequency $f_{hus}$ expressed by the following Formula (7):

$$f_{hus} = \frac{c}{L_{hus}} \qquad \text{Formula (7)}$$

is 500 Hz or more, where $L_{hus}$ is a typical length of the housing.

[13] As an embodiment of the resent disclosure, in [12], the frequency $f_{hus}$ is 1.0 kHz or more.

[14] As an embodiment of the resent disclosure, in [12] or [13], the frequency $f_{hus}$ is 2.0 kHz or more.

[15] As an embodiment of the resent disclosure, in any of [1] to [14], a frequency $f_{sub}$ expressed by the following Formula (8):

$$f_{sub} = \frac{\pi h}{2L_{sub}^2} \sqrt{\frac{Eg}{3(1-\sigma^2)\gamma}} \qquad \text{Formula (8)}$$

is 500 Hz or more, where $S_{sub}$ is an area of the substrate, E is a modulus of longitudinal elasticity of the substrate, h is a thickness of the substrate, $\sigma$ is Poisson's ratio, $\gamma$ is a dimensionless constant of 3.65, and a typical length $L_{sub}$ is a square root of the area of the substrate.

[16] As an embodiment of the resent disclosure, in [15], the frequency $f_{sub}$ is 1.0 kHz or more.

[17] As an embodiment of the resent disclosure, in [15] or [16], the frequency $f_{sub}$ is 2.0 kHz or more.

[18] As an embodiment of the resent disclosure, in any of [1] to [17], the hole is provided with a dust filter, and an acoustic characteristic impedance of the dust filter is 4000 kg/m²s or more.

[19] As an embodiment of the resent disclosure, in any of [1] to [18], the detector includes an air-suspended microstructure.

[20] As an embodiment of the resent disclosure, in any of [1] to [19], the vibration source is located inside the housing.

It is thus possible to provide an apparatus with a gas detection function capable of detecting a detection target gas with high accuracy.

DETAILED DESCRIPTION

An apparatus with a gas detection function according to an embodiment of the present disclosure will be described below, with reference to the drawings. In the drawings, the same or corresponding parts are given the same reference signs. In the following description of embodiments, the description of the same or corresponding parts is omitted or simplified as appropriate.

<Apparatus>

Figure 1:
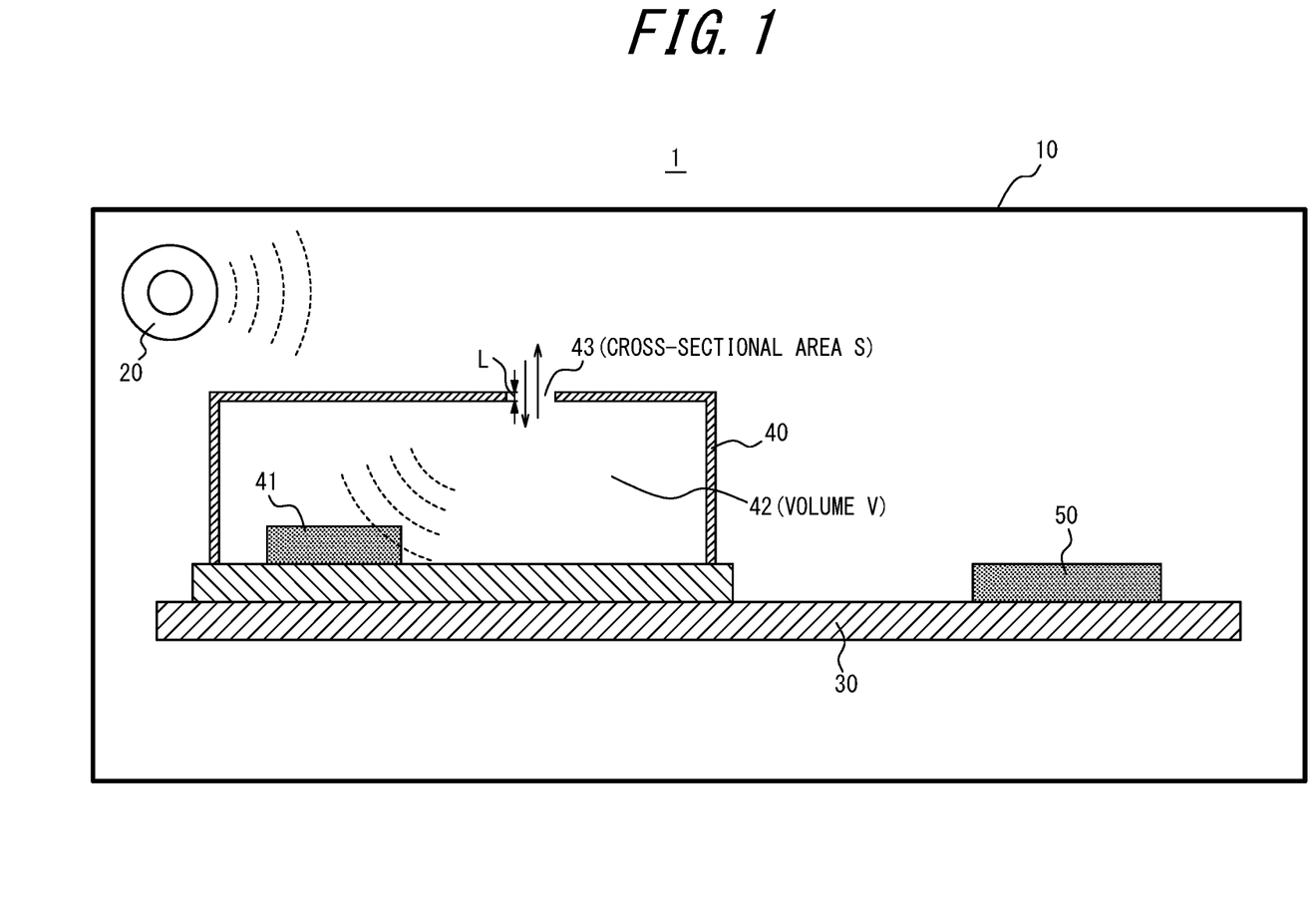
FIG. 1 is a diagram illustrating an example of the structure of an apparatus with a gas detection function according to an embodiment.

FIG. 1 is a diagram illustrating the structure of an apparatus 1 with a gas detection function according to this embodiment. The gas detection function is, for example, a function of detecting the concentration in the air of a detection target gas to be detected. The apparatus with the gas detection function includes a housing 10, a vibration source 20, a substrate 30, and a gas measurement unit 40. The gas measurement unit 40 includes a detector 41 and a gas detection space 42. The gas detection space 42 is provided with a hole 43 through which gas passes. The gas mentioned herein is, for example, air, and may include the detection target gas. In the following description, the gas is assumed to be air. The apparatus 1 may include a circuit 50 as in this embodiment. The apparatus 1 may further include a display unit such as a display.

In the apparatus 1 according to this embodiment, the vibration source 20 is attached to the housing 10, and the gas measurement unit 40 is located inside the housing 10. The gas measurement unit 40 is demarcated by a partition in the housing 10, and the gas detection space 42 is located inside the demarcated gas measurement unit 40. In the apparatus 1, the gas measurement unit 40 and the circuit 50 are arranged on the substrate 30. The gas measurement unit 40 includes the detector 41 located on the substrate 30, and the gas detection space 42 provided with the hole 43. The gas detection space 42 may be the internal space of the partition in part of which the hole 43 is formed.

The apparatus 1 is electronic equipment in particular, and includes any of various apparatuses such as electrical products. The apparatus 1 may be electronic equipment having an acoustic function of performing communication, amusement, information notification, and the like by sound such as voice and music. Specific examples of such apparatus 1 include a music player, a smart speaker, a smart home device, a smartphone, and an earphone. The apparatus 1 may be an apparatus that provides an air conditioning function. Specific examples of such apparatus 1 include an air conditioner, an air purifier, a ventilation fan, and a heating, ventilation, and air conditioning (HVAC) apparatus. The acoustic function or the air conditioning function is independently performed according to, for example, user operation, regardless of whether the gas detection function is operating. There is thus a possibility that, in the detection of the detection target gas by the gas measurement unit 40, noise increases due to the influence of irregular sound, vibration, etc. (hereinafter referred to as "unwanted sound").

<Housing>

The housing 10 is the exterior of the apparatus 1, and has a function of holding the vibration source 20. The housing 10 may also hold the substrate 30. The housing 10 may be made of metal, glass, resin, or a composite material thereof. The housing 10 may include a switch, a power connector, a communication connector, a display unit, an antenna, an input interface, a camera, a light detection and ranging (LiDAR) sensor, an infrared camera, a microphone, an indicator lamp, a fin, and the like.

<Vibration Source>

The vibration source 20 generates vibration as the acoustic function or the air conditioning function is performed. In this embodiment, the vibration source 20 emits sound. A specific example of such vibration source 20 is a speaker. Alternatively, the vibration source 20 may circulate air. A specific example of such vibration source 20 is a motor. The vibration source 20 is located outside the gas measurement unit 40. Although the vibration source 20 is attached to the housing 10 in this embodiment, the attachment position is not limited to such. For example, the vibration source 20 may be attached to the substrate 30. The vibration source 20 may be located inside or outside the housing 10.

<Substrate>

The substrate 30 has a function of holding the gas measurement unit 40. In this embodiment, the substrate 30 also holds the circuit 50. The substrate 30 may also hold the vibration source 20. The material of the substrate 30 is, for example, paper, glass cloth, polyimide film, PET film, ceramics, or the like. Examples of the resin include phenol resin, epoxy resin, polyimide resin, bismaleimide triazine resin, fluorine resin, and polyphenylene oxide resin.

<Gas Measurement Unit>

The gas measurement unit 40 detects the detection target gas. In detail, the gas measurement unit 40 measures the concentration of the detection target gas in the air, and outputs an electrical signal indicating the measurement result. The gas measurement unit 40 may be a non-dispersive infrared absorption type gas concentration measurement device having a known structure. Examples of the detection target gas include carbon dioxide, water vapor, carbon monoxide, nitrogen monoxide, ammonia, sulfur dioxide, alcohol, formaldehyde, and hydrocarbon-based gases such as methane and propane. The gas measurement unit 40 includes the detector 41, the gas detection space 42, and the hole 43.

<Detector>

The detector 41 detects changes depending on the amount of the detection target gas present, in the measurement of the concentration of the detection target gas contained in the gas (air) in the gas detection space 42. In this embodiment, the detector 41 includes a light emitting element and a light receiving element. The light emitted from the light emitting element passes through the gas detection space 42, is absorbed and attenuated depending on the amount of the detection target gas present, and is received by the light receiving element. The amount of the detection target gas present can be measured from the attenuation of the light. Examples of the light emitting element include a light emitting diode (LED), a lamp, a laser (light amplification by stimulated emission of radiation), an organic light emitting element, a microelectromechanical systems (MEMS) heater, and a vertical-cavity surface-emitting laser (VCSEL). Examples of the light receiving element include a photodiode, a phototransistor, a thermopile, a pyroelectric sensor, and a bolometer. The detector 41 may include an air-suspended microstructure using MEMS technology. The detector 41 may include a resin material, a metal package, or the like as a protective member that protects the light emitting element and the light receiving element. The detector 41 may include an optical filter that limits the wavelength of light.

As another example, the detector 41 may include a heating element and a resistor. For example, the heat generated from the heating element by applying electric current is transferred to the detection target gas in the gas detection space 42, and the temperature increase of the heating element depending on the amount of the detection target gas present is detected as a change in resistance. Examples of the heating element include a MEMS heater and a lamp. As another example, the detector 41 may include a light emitting element and a pressure sensitive element. The light emitted from the light emitting element is absorbed depending on the amount of the detection target gas present in the gas detection space 42, and the temperature, pressure, etc. of the air in the gas detection space 42 increase. The amount of the detection target gas present can be measured from the pressure increase detected by the pressure sensitive element. Examples of the pressure sensitive element include a MEMS pressure sensor and a microphone.

<Gas Detection Space>

The gas detection space 42 is separated by an outer wall, and has a function of containing gas such as air in the internal space. The gas contained in the gas detection space 42 is replaced through the hole 43. The outer wall of the gas detection space 42 is made of metal, resin, or the like.

<Hole>

The hole 43 is a hole formed in the outer wall of the gas detection space 42. Gas passes through the hole 43 and replaces the gas in the gas detection space 42. The number of holes 43 may be more than one.

Figure 2:
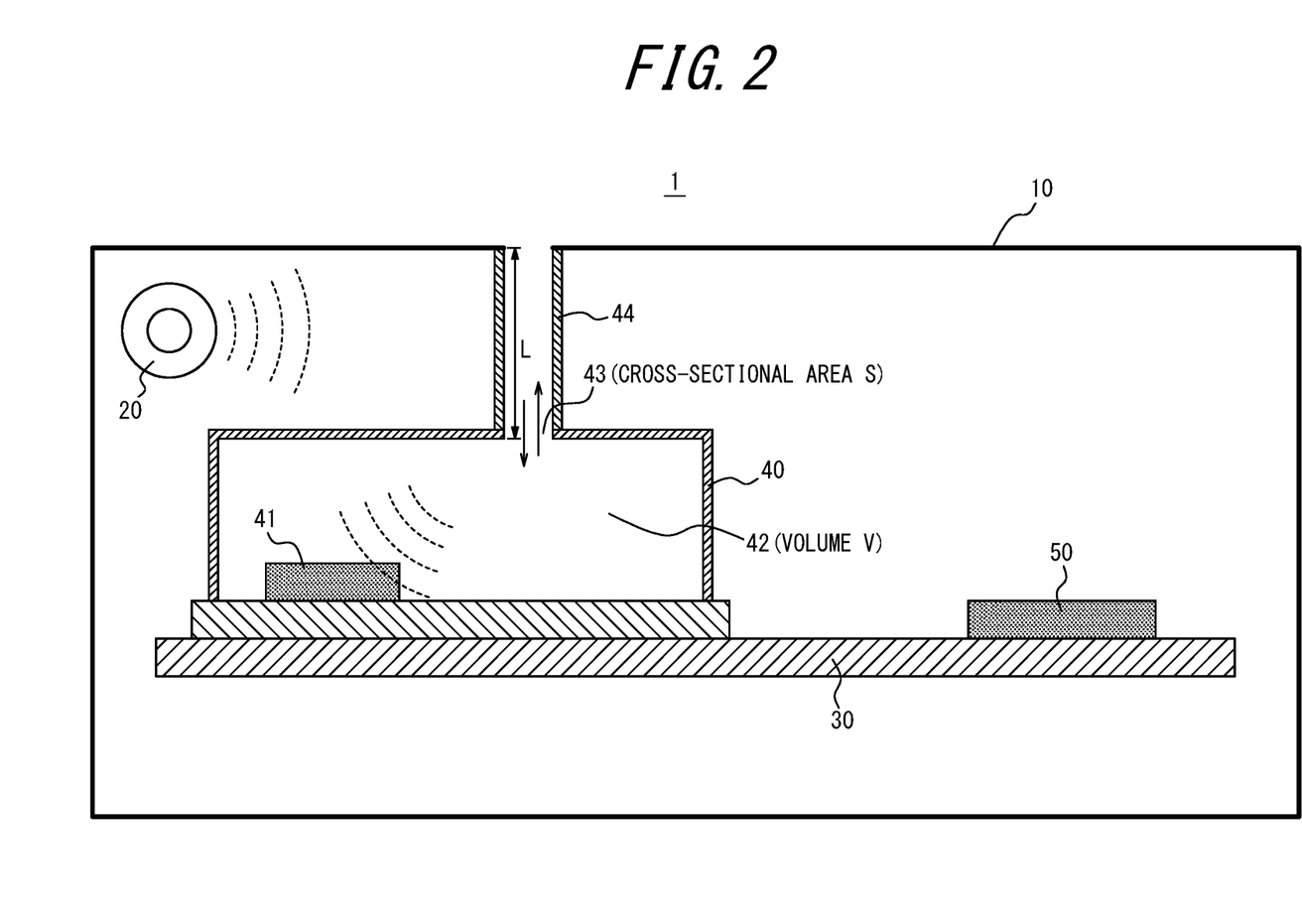
FIG. 2 is a diagram illustrating an example of the structure of an apparatus with a gas detection function in which a hole is provided with a vent pipe.
Figure 3:
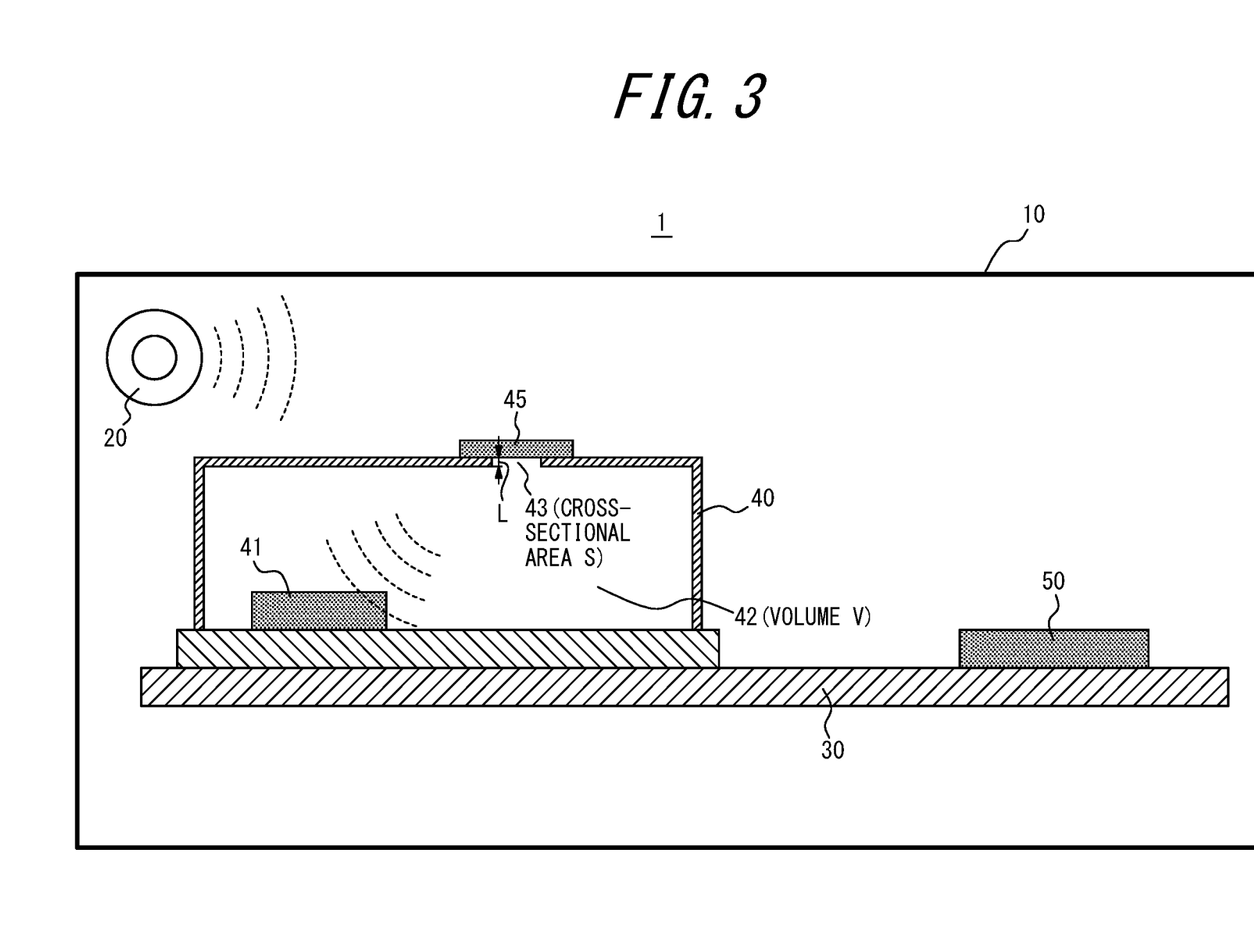
FIG. 3 is a diagram illustrating an example of the structure of an apparatus with a gas detection function in which a hole is provided with a dust filter.

As illustrated in FIG. 2, the hole 43 may be provided with a vent pipe 44. The vent pipe 44 has a function of limiting the space through which gas passes and guiding the gas to the gas detection space 42. The vent pipe 44 may be an additional part, may be a part of the housing 10 connected to the external space in a tubular shape, or may be formed by extending the hole 43 in a tubular shape. As illustrated in FIG. 3, the hole 43 may be provided with a dust filter 45 for dust prevention.

<Circuit>

The circuit 50 may control the overall apparatus 1. For example, the circuit 50 may control the vibration source 20. For example, the circuit 50 may perform computation on the output signal from the gas measurement unit 40 in order to obtain the concentration of the detection target gas. The circuit 50 may include at least one processor. The processor is, for example, a general-purpose processor or a dedicated processor specialized for specific processing. The processor is, however, not limited to such, and may be any processor.

<Explanation of Principle>

Gas is replaced, that is, taken in and out of the gas detection space 42, through the hole 43. Resonance occurs as a result of gas being taken in and out at around a specific frequency. This is the same as the Helmholtz resonance phenomenon in which a hollow musical instrument with holes, such as a guitar or an ocarina, or a bottle resonates in specific scale due to external vibration and airflow. The Helmholtz resonance phenomenon is a phenomenon in which the gas inside the cavity behaves as an air spring and the gas around the hole, as a mass, behaves as an oscillator having a resonance frequency. The gas present in the gas detection space 42 vibrates due to the Helmholtz resonance phenomenon. Coarseness and fineness caused by such vibration are detected by the detector 41 as variation in the concentration of the detection target gas, causing degradation in detection accuracy. In particular, in the case where the detector 41 includes an air-suspended microstructure, the microstructure may deform due to the vibration of the gas. This further degrades the detection accuracy.

The resonance frequency f (hereafter also simply referred to as "frequency f") of the Helmholtz resonance phenomenon depends on the volume V of the gas detection space 42, the effective length L of the hole 43, and the cross-sectional area S of the hole 43. A frequency band with high unwanted sound intensity due to music or voice in an indoor environment is a band of 100 Hz to 2.0 kHz, and has a peak around 500 Hz in particular. A frequency band with high unwanted sound intensity due to the operation of an air conditioner and the like is a band of 10 Hz to 300 Hz, and has a peak around 100 Hz in particular. As mentioned above, the apparatus 1 provides the acoustic function or the air conditioning function, and emits unwanted sound from the vibration source 20. In the case where the resonance frequency f in the gas measurement unit 40 coincides with the peak of the frequency band with high unwanted sound intensity, the Helmholtz resonance phenomenon is likely to be excited. In such a case, the detector 41 is affected and the detection accuracy degrades. In this embodiment, the structure of the gas measurement unit 40 is designed to separate the resonance frequency f from the peak wavelength of unwanted sound intensity so that the Helmholtz resonance phenomenon will not be excited. Moreover, the resonance frequency f is high in the case where the hole 43 is significantly large relative to the volume V of the gas detection space 42, according to the following Formula (9). In such a case, the detection target gas increased in temperature, pressure, etc. due to the detector 41 and the detection target gas present outside the gas detection space 42 mix quickly through the hole 43. This makes measurement difficult. Therefore, the resonance frequency f needs to be lower than a certain frequency. That is, the structure of the gas measurement unit 40 is designed so that the resonance frequency f will satisfy the condition "500 Hz<f<1 MHz". More preferably, the structure of the gas measurement unit 40 is designed to separate the resonance frequency f from the peak wavelength of unwanted sound intensity including harmonics so that the condition "1.0 kHz<f<500 kHz" will be satisfied. Further preferably, the structure of the gas measurement unit 40 is designed to separate the resonance frequency f from the frequency band with high unwanted sound intensity so that the condition "2.0 kHz<f<200 kHz" or "1 Hz<f<100 Hz" will be satisfied. The frequency f is given by the following Formula (9).

$$f = \frac{c}{2\pi}\sqrt{\frac{S}{VL}}.$$ Formula (9)

Figure 4:
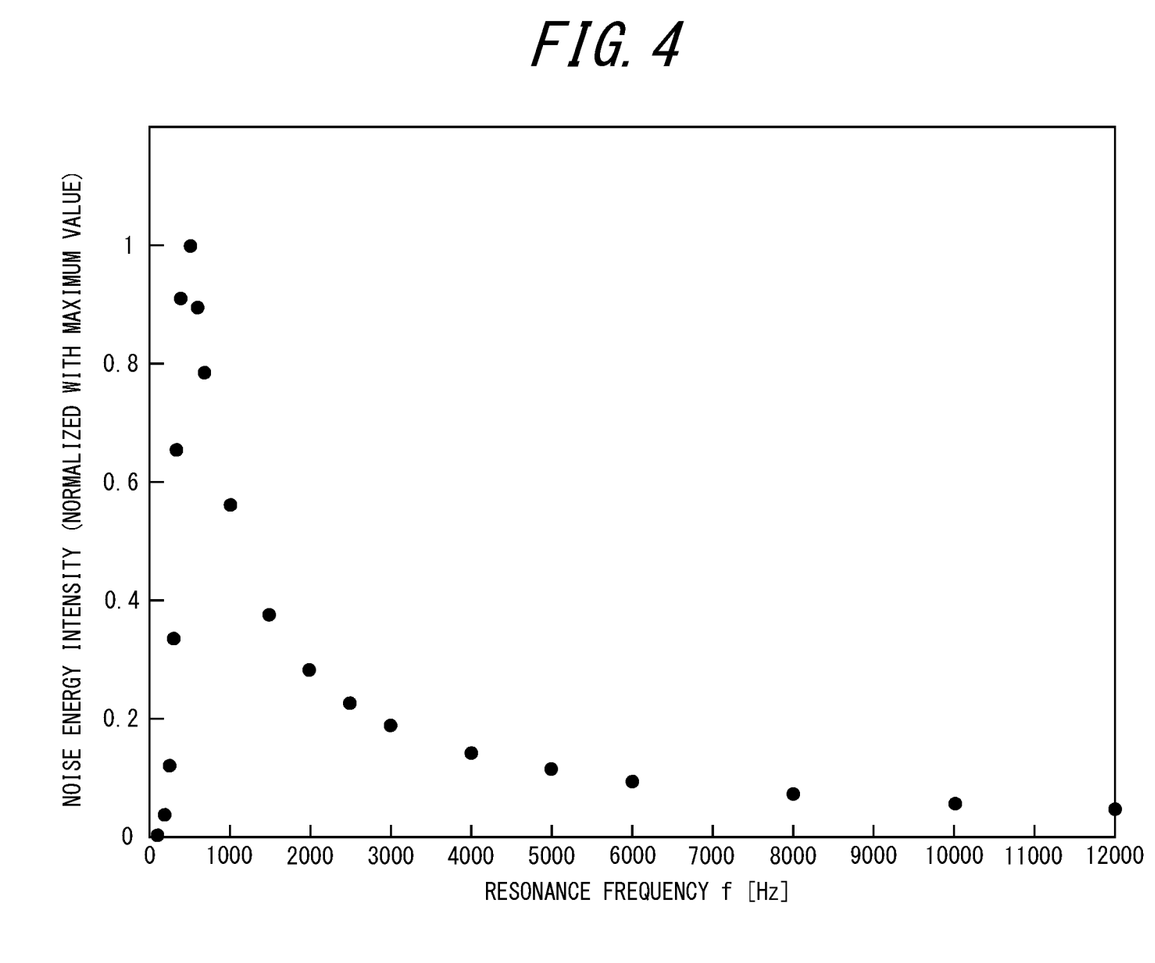
FIG. 4 is a diagram illustrating an example of noise intensity numerical calculation results.

FIG. 4 illustrates an example of numerical calculation results of noise intensity brought to the detector 41 due to the Helmholtz resonance phenomenon in the case of changing the resonance frequency f of the gas measurement unit 40. As a model of the sound emitted from the vibration source 20, the long-term average speech spectrum for Japanese of male and female talkers under the "loud" condition in FIG. 3 in reference document (Kimio Shiraishi et. al. "Amplification rationale for hearing aids based on characteristics of the Japanese language" May 15, 2021) was used. Assuming that the sound passes over the hole 43 along the gas measurement unit 40, the air vibration energy generated in the gas measurement unit 40 in the case of changing the shape of the gas measurement unit 40 to change the resonance frequency f was simulated, and the noise energy intensity brought to the detector 41 was calculated. In a cavity with a hole where the Helmholtz resonance phenomenon occurs, Lorentz distribution type excitation behavior is exhibited with respect to the resonance frequency f determined by the shape of the cavity, as in the case of forced vibration caused by application of an external force. Particularly in the case where the energy loss in the cavity is little, the excitation behavior approaches delta-function-like excitation characteristics as a result of picking up specific sound near the resonance frequency f. The model of the sound emitted from the vibration source 20 has a sharp intensity peak at around 500 Hz. The same applies to the noise energy intensity. The noise intensity can be rapidly reduced by separating the resonance frequency f away from 500 Hz.

Figure 5:
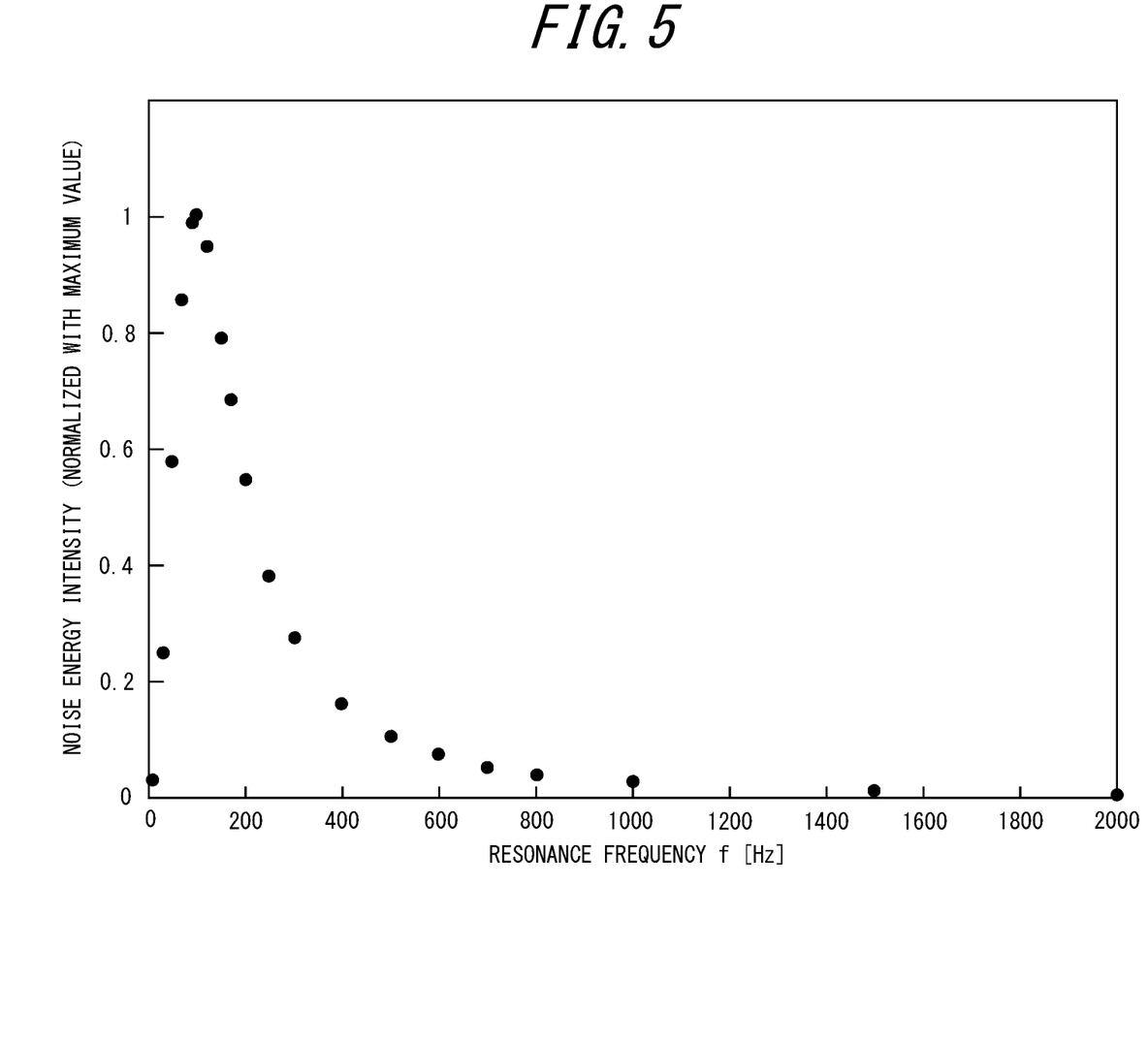
FIG. 5 is a diagram illustrating another example of noise intensity numerical calculation results.

FIG. 5 illustrates another example of numerical calculation results of noise intensity brought to the detector 41 due to the Helmholtz resonance phenomenon in the case of changing the resonance frequency f of the gas measurement unit 40. As a model of the sound emitted from the vibration source 20, measurement data of unwanted sound from the air blower during the heating operation of the Hitachi room air conditioner "RAS-AJ36D(W)" indoor unit was used. As in the example in FIG. 4, assuming that the sound passes over the hole 43 along the gas measurement unit 40, the air vibration energy generated in the case of changing the shape of the gas measurement unit 40 to change the resonance frequency f was simulated, and the noise energy intensity brought to the detector 41 was calculated. The model of the sound emitted from the vibration source 20 has a sharp intensity peak at around 100 Hz. The same applies to the noise energy intensity. The noise intensity can be rapidly reduced by separating the resonance frequency f away from 100 Hz.

In the case where the hole 43 is provided with the vent pipe 44, the cross-sectional area S is the average cross-sectional area of the hole 43 and the vent pipe 44. Moreover, c is the sound speed. For example, c is 337.7 m/s in the case of air at 10° C., 346.5 m/s in the case of air at 25° C., and 349.4 m/s in the case of air at 30° C., and is approximated by 331.5+0.61t [m/s] where t is the Celsius temperature. In the case where the concentration of the detection target gas is low, these values may be appropriately selected and used according to the room temperature. For example in the case where the concentration of the detection target gas is high, the sound speed c is given by the following Formula (10), where ρ is the density of the gas in the gas detection space 42, γ is the specific heat ratio, and p is the pressure.

$$c = \sqrt{\frac{\gamma p}{\rho}}.$$ Formula (10)

<Effective Length L>

The effective length L of the hole 43 varies depending on the shape of the hole 43 and the length L' that is the total length of the hole 43 and the vent pipe 44. In the case where the shape of the opening is circular, the effective length L is given by the following Formula (11), where a is the radius.

$L=L'+1.5a$  Formula (11).

In the case where the exit of the hole 43 and the vent pipe 44 is flat, the effective length L is given by the following Formula (12).

$L=L'+1.7a$  Formula (12).

In the case where the cross-sectional shape of the hole 43 and the vent pipe 44 is irregular, the effective length L is given by the following Formula (13), where $S_{out}$ is the area of the exit opening of the hole 43 and the vent pipe 44.

$L=L'+\sqrt{S_{out}}$  Formula (13).

For the effective length L, addition according to the shape of the opening of the hole 43 is made to the length L' obtained by combining the lengths of the hole 43 and the vent pipe 44. The addition corresponds to open end correction. In addition to the gas vibrated in the vent pipe 44, the gas around the opening also contributes to vibration. Open end correction is therefore necessary. The vibration of the gas around the opening depends on the area of the exit opening, and the gas up to the height corresponding to the square root of the area Seat contributes to vibration, as indicated in Formula (13).

The Helmholtz resonance phenomenon occurs in the case where the hole 43 is small to some extent. The Helmholtz resonance phenomenon also occurs in the case where the amount of gas in the gas detection space 42 as an air spring is greater than the amount of gas contributing to vibration as a mass. In the apparatus 1 with the gas detection function, the volume V of the gas detection space 42 is large, and the following Formula (14) holds in this embodiment.

$$V > 10LS \qquad \text{Formula (14).}$$

In order for the detector 41 to detect the detection target gas, the volume V of the gas detection space 42 needs to be sufficiently larger than the volume $V_{sen}$ of the detector 41. The following Formula (15) holds in this embodiment, where the volume $V_{sen}$ of the detector 41 is the outer size of the detector 41 and is the volume of the minimum rectangular parallelepiped including the detector 41.

$$V > 2V_{sen} \qquad \text{Formula (15).}$$

In the case where the ratio of the detector 41 to the gas detection space 42 is high, the ratio of absorption of vibration energy by Helmholtz resonance occurring in the gas measurement unit 40 is high, so that the influence of noise is significant in a small gas sensor. With such design that sets the resonance frequency f outside the unwanted sound band, the detection accuracy can be improved significantly. That is, in this embodiment, the following Formula (16) holds and desirably the following Formula (17) holds for the volume V of the gas detection space 42 relative to the volume $V_{sen}$ of the detector 41.

$$V < 400 V_{sen} \qquad \text{Formula (16).}$$

$$v < 100 V_{sen} \qquad \text{Formula (17).}$$

Particularly in the case where a thermal light source is used in the detector 41, for example, intermittent operation by turning the light source on and off at high speed cannot be performed, and accordingly the chopping frequency by chopping control cannot be increased. It is therefore difficult to separate, by frequency, the noise caused by unwanted sound and the output signal modulated by chopping. With such design that sets the resonance frequency f outside the unwanted sound band, the detection accuracy can be improved significantly. That is, in the case where the chopping frequency fc is less than 500 Hz, such design that sets the resonance frequency f outside the unwanted sound band can improve the detection accuracy significantly. In the case where a thermal light source is not used, too, the detection accuracy can be improved significantly without performing high-speed chopping control that requires a dedicated control IC for which high design technology and cost are needed.

<Arrangement of Vibration Source and Detector in Housing>

As described above, with such design that limits the range of the frequency f, the gas measurement unit 40 achieves higher detection accuracy for the detection target gas. To further enhance the detection accuracy, it is preferable to also take into account the vibration transmission path from the vibration source 20. For example, the vibration generated by the vibration source 20 is also transmitted to the detector 41 through the gas in the housing 10 and the substrate 30. It is therefore preferable to adjust the positional relationship between the vibration source 20 in the housing 10 and the detector 41 on the substrate 30 so as to weaken the vibration transmitted to the detector 41.

First, consider the transmission path through the gas in the housing 10. It is assumed that the housing 10 behaves as a resonance box. The vibration of the gas in the housing 10 increases due to the resonance mode vibration. If the vibration source 20 is located at a crest-trough position (i.e. a position with large variation) in the resonance mode, large vibration is applied to the detector 41, resulting in degradation in detection accuracy. To enhance the detection accuracy for the detection target gas, it is preferable to separate the vibration source 20 away from the crest-trough position in the resonance mode of the housing 10 and place the vibration source 20 at a node position. Since the shape is definite in the low-order mode of the resonance mode, the node position can be determined in terms of design. Specifically, in the case where the housing 10 has a rectangular parallelepiped shape, a cylindrical shape, or a spherical shape, the plane of symmetry, the axis of symmetry, or the center point is a node in the resonance mode of sound pressure. For example, the center between a pair of facing surfaces is a node. By placing the vibration source 20 at such a position, the amount of vibration transmitted from the vibration source 20 to the detector 41 is reduced, with it being possible to improve the detection accuracy of the apparatus 1.

The crest-to-crest length in the resonance mode is determined by the size of the housing 10. Let $V_{hus}$ be the volume of the housing 10, and typical length $L_{hus}$ be the cube root of the volume $V_{hus}$ or the distance from the inner wall surface of the housing 10 to the node. Then, the detector 41 is placed at a position of $L_{hus}/10$ from the node position in the length in a certain direction. The typical length $L_{hus}$ varies according to the shape of the housing 10, and may be the cube root in the case where the side lengths of the housing 10 are equal in three directions, and the distance from the inner wall surface to the node in the case where the housing 10 has any other shape.

The edge parts of the housing 10 are each a crest position in the resonance mode. By placing the vibration source 20 at a position other than the edge parts of the housing 10, the amount of vibration transmitted from the vibration source 20 to the detector 41 is reduced, with it being possible to improve the detection accuracy of the apparatus 1. For example, the detector 41 is placed at a position inward from an edge of the housing 10 by more than $L_{hus}/5$.

The housing 10 may have a shape more complex than a rectangular parallelepiped, a cylinder, or a sphere. Since the behavior in the low-order resonance mode is qualitatively the same, however, it suffices to approximate the housing 10 by a rectangular parallelepiped, a cylinder, or a sphere so as to minimize the volume error, and place the vibration source 20 or the detector 41 not at a crest position but at a node position in the defined shape. For example, the vibration source 20 or the detector 41 may be located at the plane of symmetry (node position) of a rectangular parallelepiped approximately defined for the housing 10. For example, the vibration source 20 or the detector 41 may be located at the axis of symmetry (node position) of a cylinder approximately defined for the housing 10. For example, the vibration source 20 or the detector 41 may be located at the center point (node position) of a sphere approximately defined for the housing 10.

<Arrangement of Vibration Source and Detector on Substrate>

In the case where the periphery of the substrate 30 is fixed, the substrate 30 behaves as a resonance plate whose periphery does not vibrate. If the vibration source 20 is located at a crest-trough position in the resonance mode, energy is efficiently transferred for the resonance mode vibration of the vibration of the substrate 30. In such a case, the vibration of the substrate 30 increases, and the vibration is applied to the detector 41 through the substrate 30. The vibration is detected by the detector 41 as an electric signal, resulting in degradation in detection accuracy. Moreover, if the detector 41 is located at a crest-trough position in the resonance mode, large vibration is applied to the detector 41. The vibration is detected by the detector 41 as an electric signal, resulting in degradation in detection accuracy.

From the resonance mode analysis of a rectangular plate or a circular plate, each end or the axis of symmetry of the substrate 30 is a node. By placing the vibration source 20 or the detector 41 at such a node position, the amount of vibration transmitted from the vibration source 20 to the detector 41 is reduced, with it being possible to improve the detection accuracy of the apparatus 1.

The crest-to-crest length in the resonance mode is determined by the size of the substrate 30. Let $S_{sub}$ be the area of the substrate 30, and typical length $L_{sub}$ be the square root of the area $S_{sub}$. Then, the vibration source 20 or the detector 41 is placed at a position of $L_{sub}/10$ from the node position.

The center part of the substrate 30 is a crest position in the resonance mode. By placing the vibration source 20 at a position other than the center part of the substrate 30, the amount of vibration transmitted from the vibration source 20 to the detector 41 is reduced, with it being possible to improve the detection accuracy of the apparatus 1. For example, the vibration source 20 or the detector 41 is placed at a position outward from the center part of the substrate 30 by more than $L_{sub}/10$.

The substrate 30 may have a shape more complex than a rectangular or circular plate. Since the behavior in the low-order resonance mode is qualitatively the same, however, it suffices to approximate the substrate 30 by a rectangular or circular plate so as to minimize the volume error, and place the vibration source 20 or the detector 41 not at a crest position but at a node position in the defined shape. For example, the vibration source 20 or the detector 41 may be located at an end of a rectangle approximately defined for the substrate 30.

<Size of Housing>

The housing 10 has a resonance mode of the lowest order of frequency $f_{hus}$ approximately represented by the following Formula (18), from resonance mode analysis in the case of a rectangular parallelepiped. By setting the frequency $f_{hus}$ outside the frequency band with high unwanted sound intensity or the frequency band with high unwanted sound intensity due to driving of an air conditioner, the vibration applied to the detector 41 can be reduced to thus improve the detection accuracy of the apparatus 1 for the detection target gas.

$$f_{hus} = \frac{c}{L_{hus}}. \qquad \text{Formula (18)}$$

$f_{hus}$ is preferably 500 Hz or more. $f_{hus}$ is more preferably 1.0 kHz or more. $f_{hus}$ is further preferably 2.0 kHz or more. $f_{hus}$ is preferably 100 Hz or less.

<Size of Substrate>

The substrate 30 has a resonance mode of the lowest order of frequency $f_{sub}$ approximately represented by the following Formula (19), from resonance mode analysis in the case of a rectangular plate. By setting the frequency $f_{sub}$ outside the frequency band with high unwanted sound intensity or the frequency band with high unwanted sound intensity due to driving of an air conditioner, the vibration applied to the detector 41 can be reduced to thus improve the detection accuracy of the apparatus 1 for the detection target gas.

$$f_{sub} = \frac{\pi h}{2 L_{sub}^2} \sqrt{\frac{Eg}{3(1-\sigma^2)\gamma}}. \qquad \text{Formula (19)}$$

Here, E is the modulus of longitudinal elasticity, g is the gravitational acceleration and is given by 9.80665 m/s², σ is Poisson's ratio, h is the thickness of the substrate 30, and γ is a dimensionless constant given by 3.65. $f_{sub}$ is preferably 500 Hz or more. $f_{sub}$ is more preferably 1.0 kHz or more. $f_{sub}$ is further preferably 2.0 kHz or more. $f_{sub}$ is preferably 100 Hz or less.

<Dust Filter>

The hole 43 may be provided with the dust filter 45. The dust filter 45 reflects or attenuates the vibration (sound) of gas in the gas detection space 42, thereby suppressing the vibration applied to the detector 41. The detection accuracy of the apparatus 1 can thus be improved. When the acoustic characteristic impedance of the dust filter 45 is higher, the reflection or attenuation performance of the dust filter 45 is higher. The acoustic characteristic impedance is preferably 4000 kg/m²s or more, which is sufficiently larger than the impedance of air, i.e. approximately 10 times or more the impedance of air. The acoustic characteristic impedance is more preferably 40000 kg/m²s or more. The acoustic characteristic impedance is given by the product of the medium density ρm [kg/m³] and the sound speed Cm in the medium.

As described above, the apparatus with the gas detection function according to this embodiment having the foregoing structure can detect the detection target gas with high accuracy by suppressing vibration that affects the gas measurement unit 40.

While the embodiments of the present disclosure have been described by way of the drawings and examples, various changes and modifications may be easily made by those of ordinary skill in the art based on the present disclosure. Such changes and modifications are therefore included in the scope of the present disclosure. For example, the functions included in the components, etc. may be rearranged without logical inconsistency, and a plurality of components, etc. may be combined into one component, etc. and a component, etc. may be divided into a plurality of components, etc.

The invention claimed is:

1. An apparatus with a gas detection function, comprising:
a housing;
a vibration source; and
a gas measurement unit located inside the housing and demarcated by a partition,
wherein the vibration source is located outside the gas measurement unit,
the gas measurement unit includes a detector located on a substrate, and a gas detection space provided with a hole through which a gas passes, and a frequency f expressed by the following Formula (1):

$$f = \frac{c}{2\pi}\sqrt{\frac{S}{VL}} \qquad \text{Formula (1)}$$

is 500 Hz or more, where V is a volume of the gas detection space, S is a cross-sectional area of the hole, L is an effective length of the hole, and c is a sound speed.

2. The apparatus with a gas detection function according to claim 1, wherein the hole is provided with a vent pipe, and the effective length is given by the following Formula (2):

$$L = L' + 1.5a \qquad \text{Formula (2),}$$

where L' is a total length of the hole and the vent pipe, and a is a radius of the hole.

3. The apparatus with a gas detection function according to claim 1, wherein the hole is provided with a vent pipe, an exit of the hole and the vent pipe is flat, and the effective length is given by the following Formula (3):

$$L = L' + 1.7a \qquad \text{Formula (3),}$$

where L' is a total length of the hole and the vent pipe, and a is a radius of the hole.

4. The apparatus with a gas detection function according to claim 1, wherein the hole is provided with a vent pipe, a cross-sectional shape of the hole and the vent pipe is irregular, and the effective length is given by the following Formula (4):

$$L = L' + \sqrt{S_{out}} \qquad \text{Formula (4),}$$

where L' is a total length of the hole and the vent pipe, and $S_{out}$ is an area of an exit opening of the hole and the vent pipe.

5. The apparatus with a gas detection function according to claim 1, wherein the frequency f is 1.0 kHz or more.

6. The apparatus with a gas detection function according to claim 1, wherein the frequency f is 2.0 kHz or more.

7. An apparatus with a gas detection function, comprising:
a housing;
a vibration source; and
a gas measurement unit located inside the housing,
wherein the gas measurement unit includes a detector located on a substrate, and a gas detection space provided with a hole through which a gas passes,
the hole is provided with a vent pipe,
a cross-sectional shape of the hole and the vent pipe is irregular,
an effective length L of the hole is given by the following Formula (5):

$$L = L' + \sqrt{S_{out}} \qquad \text{Formula (5),}$$

where L' is a total length of the hole and the vent pipe, and $S_{out}$ is an area of an exit opening of the hole and the vent pipe, and
a frequency f expressed by the following Formula (6):

$$f = \frac{c}{2\pi}\sqrt{\frac{S}{VL}} \qquad \text{Formula (6)}$$

is 100 Hz or less, where V is a volume of the gas detection space, S is a cross-sectional area of the hole, and c is a sound speed.

8. The apparatus with a gas detection function according to claim 1, wherein the vibration source or the detector is located at a plane of symmetry of a rectangular parallelepiped approximately defined for the housing.

9. The apparatus with a gas detection function according to claim 1, wherein the vibration source or the detector is located at an axis of symmetry of a cylinder approximately defined for the housing.

10. The apparatus with a gas detection function according to claim 1, wherein the vibration source or the detector is located at a center point of a sphere approximately defined for the housing.

11. The apparatus with a gas detection function according to claim 1, wherein the vibration source or the detector is located at an end of a rectangle approximately defined for the substrate.

12. The apparatus with a gas detection function according to claim 1, wherein a frequency $f_{hus}$ expressed by the following Formula (7):

$$f_{hus} = \frac{c}{L_{hus}} \qquad \text{Formula (7)}$$

is 500 Hz or more, where $L_{hus}$ is a typical length of the housing.

13. The apparatus with a gas detection function according to claim 12, wherein the frequency $f_{hus}$ is 1.0 kHz or more.

14. The apparatus with a gas detection function according to claim 12, wherein the frequency $f_{hus}$ is 2.0 kHz or more.

15. The apparatus with a gas detection function according to claim 1, wherein a frequency $f_{sub}$ expressed by the following Formula (8):

$$f_{sub} = \frac{\pi h}{2 L_{sub}^2}\sqrt{\frac{Eg}{3(1-\sigma^2)\gamma}} \qquad \text{Formula (8)}$$

is 500 Hz or more, where $S_{sub}$ is an area of the substrate, E is a modulus of longitudinal elasticity of the substrate, h is a thickness of the substrate, $\sigma$ is Poisson's ratio, $\gamma$ is a dimensionless constant of 3.65, and a typical length $L_{sub}$ is a square root of the area of the substrate.

16. The apparatus with a gas detection function according to claim 15, wherein the frequency $f_{sub}$ is 1.0 kHz or more.

17. The apparatus with a gas detection function according to claim 15, wherein the frequency $f_{sub}$ is 2.0 kHz or more.

18. The apparatus with a gas detection function according to claim 1, wherein the hole is provided with a dust filter, and an acoustic characteristic impedance of the dust filter is 4000 kg/m$^2$s or more.

19. The apparatus with a gas detection function according to claim 1, wherein the detector includes an air-suspended microstructure.

20. The apparatus with a gas detection function according to claim 1, wherein the vibration source is located inside the housing.

* * * * *